US011076990B2

(12) United States Patent
Lee et al.

(10) Patent No.: US 11,076,990 B2
(45) Date of Patent: Aug. 3, 2021

(54) SYSTEM AND METHOD FOR OPHTHALMIC LASER SURGERY EMPLOYING EYE TRACKING WITHOUT EYE DOCKING

(71) Applicant: AMO DEVELOPMENT, LLC, Santa Ana, CA (US)

(72) Inventors: Hon M. Lee, Ladera Ranch, CA (US); Peter-Patrick De Guzman, Orange, CA (US); Victor Kardos, Irvine, CA (US); Hong Fu, Pleasanton, CA (US); Robert G. Heitel, Laguna Beach, CA (US); John M. Tamkin, San Marino, CA (US); Mikhail Levin, Santa Ana, CA (US); Bing Wang, Corona, CA (US)

(73) Assignee: AMO Development, LLC, Santa Ana, CA (US)

( * ) Notice: Subject to any disclaimer, the term of this patent is extended or adjusted under 35 U.S.C. 154(b) by 401 days.

(21) Appl. No.: 15/847,897

(22) Filed: Dec. 19, 2017

(65) Prior Publication Data
US 2018/0110647 A1   Apr. 26, 2018

Related U.S. Application Data

(62) Division of application No. 14/198,394, filed on Mar. 5, 2014, now abandoned.
(Continued)

(51) Int. Cl.
*A61F 9/008* (2006.01)
(52) U.S. Cl.
CPC .......... *A61F 9/008* (2013.01); *A61F 9/00825* (2013.01); *A61F 2009/00846* (2013.01); *A61F 2009/00851* (2013.01)

(58) Field of Classification Search
CPC ............................................... A61F 9/008–009
See application file for complete search history.

(56) References Cited

U.S. PATENT DOCUMENTS

| 4,764,930 A | 8/1988 | Bille et al. |
| 5,549,632 A | 8/1996 | Lai |

(Continued)

FOREIGN PATENT DOCUMENTS

| WO | 2004084719 A1 | 10/2004 |
| WO | 2012170966 A1 | 12/2012 |

OTHER PUBLICATIONS

Co-pending U.S. Appl. No. 13/230,590, filed Sep. 12, 2011.
(Continued)

*Primary Examiner* — Nathan J Jenness
(74) *Attorney, Agent, or Firm* — Johnson & Johnson Surgical Vision, Inc.

(57) ABSTRACT

A system and method for performing ophthalmic surgery using an ultra-short pulsed laser is provided. The system includes a laser engine configured to provide an ultra-short pulsed laser beam, optics configured to direct the laser beam to an undocked eye of a patient, an eye tracker configured to measure five degrees of freedom of movement of the undocked eye, an optical coherence tomography module configured to measure depth of the undocked eye, and a controller configured to control laser beam position on the undocked eye toward a desired laser pattern based on depth and the five degrees of freedom of movement of the undocked eye. Adaptive optics are also provided. Also disclosed are a scleral ring including fiducial markings and a compliant contact lens and fluid tillable contact lens configured to facilitate ultra-short pulsed laser surgery while reducing or eliminating eye docking requirements.

4 Claims, 12 Drawing Sheets

Related U.S. Application Data

(60) Provisional application No. 61/799,434, filed on Mar. 15, 2013.

(56) References Cited

U.S. PATENT DOCUMENTS

| | | | |
|---|---|---|---|
| 5,984,916 A | 11/1999 | Lai | |
| 5,993,438 A | 11/1999 | Juhasz et al. | |
| 6,019,472 A * | 2/2000 | Koester | A61B 3/125 |
| | | | 351/219 |
| 6,299,307 B1 | 10/2001 | Oltean et al. | |
| 6,325,792 B1 | 12/2001 | Swinger et al. | |
| D462,442 S | 9/2002 | Webb | |
| 6,623,476 B2 | 9/2003 | Kurtz et al. | |
| 6,863,667 B2 | 3/2005 | Webb et al. | |
| 2003/0153904 A1* | 8/2003 | Patel | A61F 9/00802 |
| | | | 606/5 |
| 2005/0024586 A1 | 2/2005 | Teiwes et al. | |
| 2005/0273185 A1 | 12/2005 | Teiwes et al. | |
| 2006/0023162 A1 | 2/2006 | Azar et al. | |
| 2007/0179478 A1 | 8/2007 | Dobschal et al. | |
| 2007/0252951 A1 | 11/2007 | Hammer et al. | |
| 2008/0078752 A1 | 4/2008 | Bischoff et al. | |
| 2008/0086048 A1* | 4/2008 | Dupps, Jr. | A61B 3/165 |
| | | | 600/405 |
| 2009/0137989 A1* | 5/2009 | Kataoka | A61F 9/009 |
| | | | 606/5 |
| 2009/0275929 A1 | 11/2009 | Zickler | |
| 2010/0022994 A1 | 1/2010 | Frey et al. | |
| 2010/0274228 A1* | 10/2010 | Mrochen | A61F 9/013 |
| | | | 604/541 |
| 2011/0118712 A1 | 5/2011 | Lubatschowski et al. | |
| 2011/0144628 A1 | 6/2011 | Vogler | |
| 2011/0319873 A1* | 12/2011 | Raksi | A61F 9/009 |
| | | | 606/1 |
| 2013/0226158 A1* | 8/2013 | Rathjen | A61F 9/00831 |
| | | | 606/4 |
| 2014/0114297 A1* | 4/2014 | Woodley | A61F 9/008 |
| | | | 606/6 |

OTHER PUBLICATIONS

Fuensanta A., et al., "The Human Eye and Adaptive Optics, Topics in Adaptive Optics", Dr. Bob Tyson (Ed.), Jan. 20, 2012, ISBN: 978-953-307-949-3.

Hansen A., et al., "Lowering Threshold Energy for Femtosecond Laser Pulse Photodisruption Through Turbid Media Using Adaptive Optics," SPIE, 2011, vol. 7885, pp. 78850Q.

International Search Report and Written Opinion for Application No. PCT/US2014/020861, dated Nov. 11, 2014, 14 pages.

Ortiz S., et al., "Corneal Topography from Spectral Optical Coherence Tomography (sOCT)," Journal of Biomedical Optics Express, 2011, vol. 2 (12), pp. 3232-3247.

\* cited by examiner

801

802

803

804

805

806

807

808

809

810

SYSTEM AND METHOD FOR OPHTHALMIC LASER SURGERY EMPLOYING EYE TRACKING WITHOUT EYE DOCKING

CROSS-REFERENCES TO RELATED APPLICATIONS

This application is a Divisional under 35 U.S.C. § 121 of U.S. patent application Ser. No. 14/198,394, filed Mar. 5, 2014, which claims priority to U.S. provisional application No. 61/799,434 filed on Mar. 15, 2013. The entire contents of the above-referenced applications are incorporated herein by reference.

BACKGROUND

Field

Embodiments of this invention generally relate to ophthalmic surgical techniques, and more particularly to a surgical laser system using an ultra-short pulsed laser for refractive and cataract procedures without docking a patient's eye.

Background

Eye surgery is now commonplace with some patients pursuing it as an elective procedure to avoid using contact lenses or glasses and others pursuing it to correct adverse conditions such as cataracts. Moreover, with recent developments in laser technology, laser surgery has become the technique of choice for ophthalmic procedures. Laser eye surgery typically uses different types of laser beams, such as ultraviolet lasers, infrared lasers, and near-infrared, ultra-short pulsed lasers, for various procedures and indications.

A surgical laser beam is preferred over manual tools like microkeratomes as it can be focused accurately on extremely small amounts of ocular tissue, thereby enhancing precision and reliability. For example, in the commonly-known LASIK (Laser Assisted In Situ Keratomileusis) procedure, an ultra-short pulsed laser is used to cut a corneal flap to expose the corneal stroma for photoablation with an excimer laser. Ultra-short pulsed lasers emit radiation with pulse durations as short as 10 femtoseconds and as long as 3 nanoseconds, and a wavelength between 300 nm and 3000 nm. Besides cutting corneal flaps, ultra-short pulsed lasers are used to perform cataract-related surgical procedures, including capsulorhexis, anterior and posterior capsulotomy, as well as softening and/or breaking of the cataractous lens.

Laser eye surgery is performed while the patient is in a reclined position but awake, meaning that the patient's eyes are moving during the procedure. As would be expected, patient eye movement relative to the laser beam's focal point can undermine the laser's accuracy and precision, and may even result in permanent tissue damage.

Hence, these types of surgeries may require use of a device called an eye stabilizer or patient interface, commonly called "docking" of the eye. Examples of ophthalmic patient interface devices used for "docking" the eye are described in U.S. Pat. No. 6,863,667, issued to Webb et al., U.S. Pat. No. D462,442 issued to Webb, U.S. Pat. No. 6,623,476, issued to Juhasz et al., and co-pending U.S. patent application Ser. No. 13/230,590, which are incorporated here by reference. While these devices effectively restrain eye movement, and provide a positional reference mechanism enabling the surgeon to deliver the laser to the eye with accuracy, they have certain challenges. A common complaint is that the mechanical pressure or vacuum suction used to attach the interfacing device to the eye causes discomfort and may contribute to post-operative pain and hemorrhaging. Another complaint is that patient discomfort and corneal wrinkling are exacerbated when the interfacing device uses a rigid contact lens to applanate or flatten the cornea as part of the surgical procedure.

Eye tracking systems and devices monitor the position of a selected feature of the eye and provide the laser system with real time signals about any displacement in the position as a result of movement during surgery. Then, as necessary, the surgical laser system uses the signals to adjust or re-position the focal point of the laser beam before making an incision. Some examples of eye tracking systems and techniques are disclosed in U.S. Pat. No. 6,299,307, issued to Oltean et al., which is incorporated here by reference. In general, however, the delays inherent in eye trackers, coupled with the high speed and degree of precision required for incisions in procedures using ultra-short pulsed lasers, as well as the difficulty in accurately tracking the eye using an eye tracker can result in less than ideal cuts.

Issues with performing any type of laser cataract or refractive ocular surgery without a docking mechanism or eye stabilizer include the uncertainty of the position and orientation of the eye at any point in time. Compounding this issue is the fact that eyes tend to have different sizes, shapes, and textures in different individuals, and certain aspects of the eye, such as the cornea and iris, change in color in an individual eye. As a result, it can be difficult to quickly resolve and discern components of the eye using an eye tracker.

Additional issues when using a docking mechanism include index of refraction issues, wherein a laser provided to an eye can, in certain instances, make an imperfect cut as a result of the refractive index of the light energy in air significantly differing from that of the ocular tissue, occasionally resulting in beam reflection or scattering. Further, use of a docking mechanism can increase intraocular pressure and can cause corneal wrinkles that distort the laser beam.

In view of these challenges, there is a need for an ultra-short pulsed laser surgical system that minimizes or eliminates the need for eye stabilization equipment, and/or decreases the patient discomfort when eye stabilization equipment is used, wherein the ultra-short pulsed surgical laser system without a "docking" arrangement or with limited eye stabilization provides robust and accurate cuts during refractive and cataract procedures.

SUMMARY

A system and method for performing ophthalmic surgery using an ultra-short pulsed laser is provided. The surgical laser system includes a laser engine configured to provide an ultra-short pulsed laser beam; optics configured to direct the laser beam to an undocked eye of a patient; an eye tracker configured to measure five degrees of freedom of movement of the undocked eye; an optical coherence tomography module configured to measure depth of the undocked eye; and a controller configured to control laser beam position on the undocked eye toward a desired laser pattern based on depth and the five degrees of freedom of movement of the undocked eye. Adaptive optics are also provided. Also disclosed are a scleral ring with fiducial markings and a compliant contact lens and fluid-fillable contact lens configured to facilitate ultra-short pulsed laser surgery while reducing or eliminating eye docking requirements.

This summary and the following detailed description are merely exemplary, illustrative, and explanatory, and are not intended to limit, but to provide further explanation of the invention as claimed. Additional features and advantages of the invention will be set forth in the descriptions that follow, and in part will be apparent from the description, or may be learned by practice of the invention. The objectives and other advantages of the invention will be realized and attained by the structure particularly pointed out in the written description, claims and the appended drawings.

DETAILED DESCRIPTION

The drawings and related descriptions of the embodiments have been simplified to illustrate elements that are relevant for a clear understanding of these embodiments, while eliminating various other elements found in conventional collagen shields, ophthalmic patient interfaces, and in laser eye surgical systems. Those of ordinary skill in the art may thus recognize that other elements and/or steps are desirable and/or required in implementing the embodiments that are claimed and described. But, because those other elements and steps are well known in the art, and because they do not necessarily facilitate a better understanding of the embodiments, they are not discussed. This disclosure is directed to all applicable variations, modifications, changes, and implementations known to those skilled in the art. As such, the following detailed descriptions are merely illustrative and exemplary in nature and are not intended to limit the embodiments of the subject matter or the uses of such embodiments. As used in this application, the terms "exemplary" and "illustrative" mean "serving as an example, instance, or illustration." Any implementation described as exemplary or illustrative is not meant to be construed as preferred or advantageous over other implementations. Further, there is no intention to be bound by any expressed or implied theory presented in the preceding background of the invention, brief summary, or the following detailed description.

Figure 1:
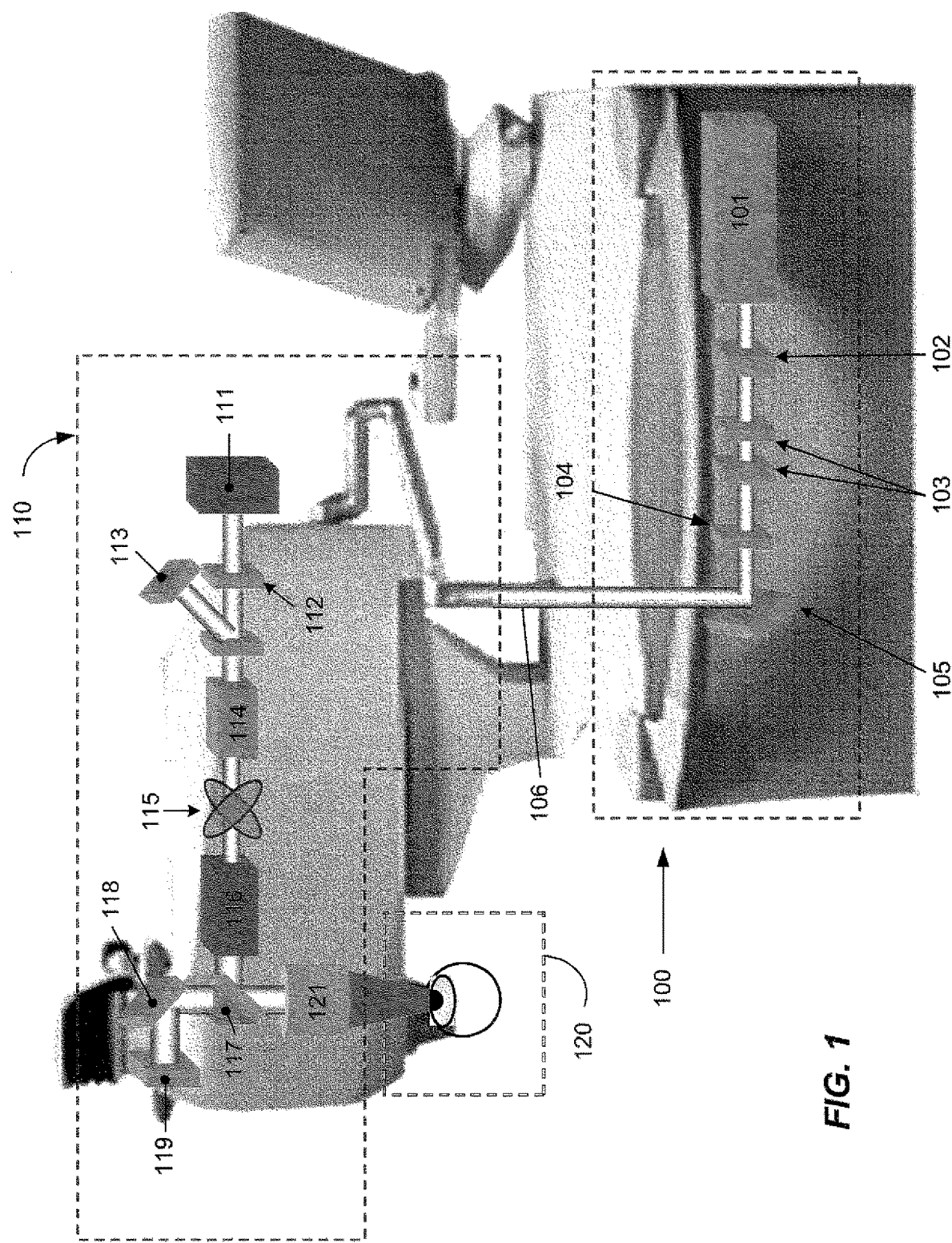
FIG. 1 illustrates a general overview of a ultra-short pulsed laser arrangement configured to employ the present design.

FIG. 1 illustrates a general overview of an ultra-short pulsed laser arrangement configured to employ the present design. From FIG. 1, laser engine 100 includes laser source 101 provides laser light to variable attenuator 102 configured to attenuate the beam, then to energy monitors 103 to monitor beam energy level, and first safety shutter 104 serving as a shutoff device if the beam is unacceptable. Beam steering mirror 105 redirects the resultant laser beam to the beam delivery device 110, through articulated arm 106 to range finding camera 111. The range finding camera 111 determines the range needed for the desired focus at the eye 120. Beam delivery device 110 includes second safety shutter 112 and beam monitor 113, beam pre-expander 114, X-Y (position) scanner 115, and zoom beam expander 116. Zoom beam expander 116 expands the beam toward IR mirror 117 which reflects and transmits the received beam. Mirror 118 reflects the received beam to video camera 119, which records the surgical procedure on the eye 120. IR mirror 117 also reflects the laser light energy to objective lens 121, which focuses laser light energy to eye 120

In ophthalmic surgery using a pulsed laser beam, non-ultraviolet (UV), ultra-short pulsed laser technology can produce pulsed laser beams having pulse durations measured in femtoseconds. Such a device as shown in FIG. 1 can provide an intrastromal photodisruption technique for reshaping the cornea using a non-UV, ultra-short (e.g., femtosecond or picosecond pulse duration), pulsed laser beam produced by laser source 101 that propagates through corneal tissue and is focused at a point below the surface of the cornea to photodisrupt stromal tissue at the focal point.

Although the system may be used to photoalter a variety of materials (e.g., organic, inorganic, or a combination thereof), the system is suitable for ophthalmic applications in one embodiment. The focusing optics, such as beam pre-expander 114, zoom beam expander 116, IR mirror 117 and objective lens 121, direct the pulsed laser beam toward an eye 120 (e.g., onto or into a cornea) for plasma mediated (e.g., non-UV) photoablation of superficial tissue, or into the stroma of the cornea for intrastromal photodisruption of tissue. In this embodiment, the system may also include a lens to change the shape (e.g., flatten or curve) of the cornea prior to scanning the pulsed laser beam toward the eye. The system is capable of generating the pulsed laser beam with physical characteristics similar to those of the laser beams generated by a laser system disclosed in U.S. Pat. Nos. 4,764,930 and 5,993,438, which are incorporated here by reference.

The ophthalmic laser system can produce an ultra-short pulsed laser beam for use as an incising laser beam. This pulsed laser beam preferably has laser pulses with durations as long as a few nanoseconds or as short as a few femtoseconds. For intrastromal photodisruption of the tissue, the pulsed laser beam has a wavelength that permits the pulsed laser beam to pass through the cornea without absorption by the corneal tissue. The wavelength of the pulsed laser beam is generally in the range of about 400 nm to about 3000 nm, and the irradiance of the pulsed laser beam for accomplishing photodisruption of stromal tissues at the focal point is typically greater than the threshold for optical breakdown of the tissue. Although a non-UV, ultra-short pulsed laser beam is described in this embodiment, the pulsed laser beam may have other pulse durations and different wavelengths in other embodiments. Further examples of devices employed in performing ophthalmic laser surgery are disclosed in, for example, U.S. Pat. Nos. 5,549,632, 5,984,916, and 6,325,792, which are incorporated here by reference.

Figure 2:
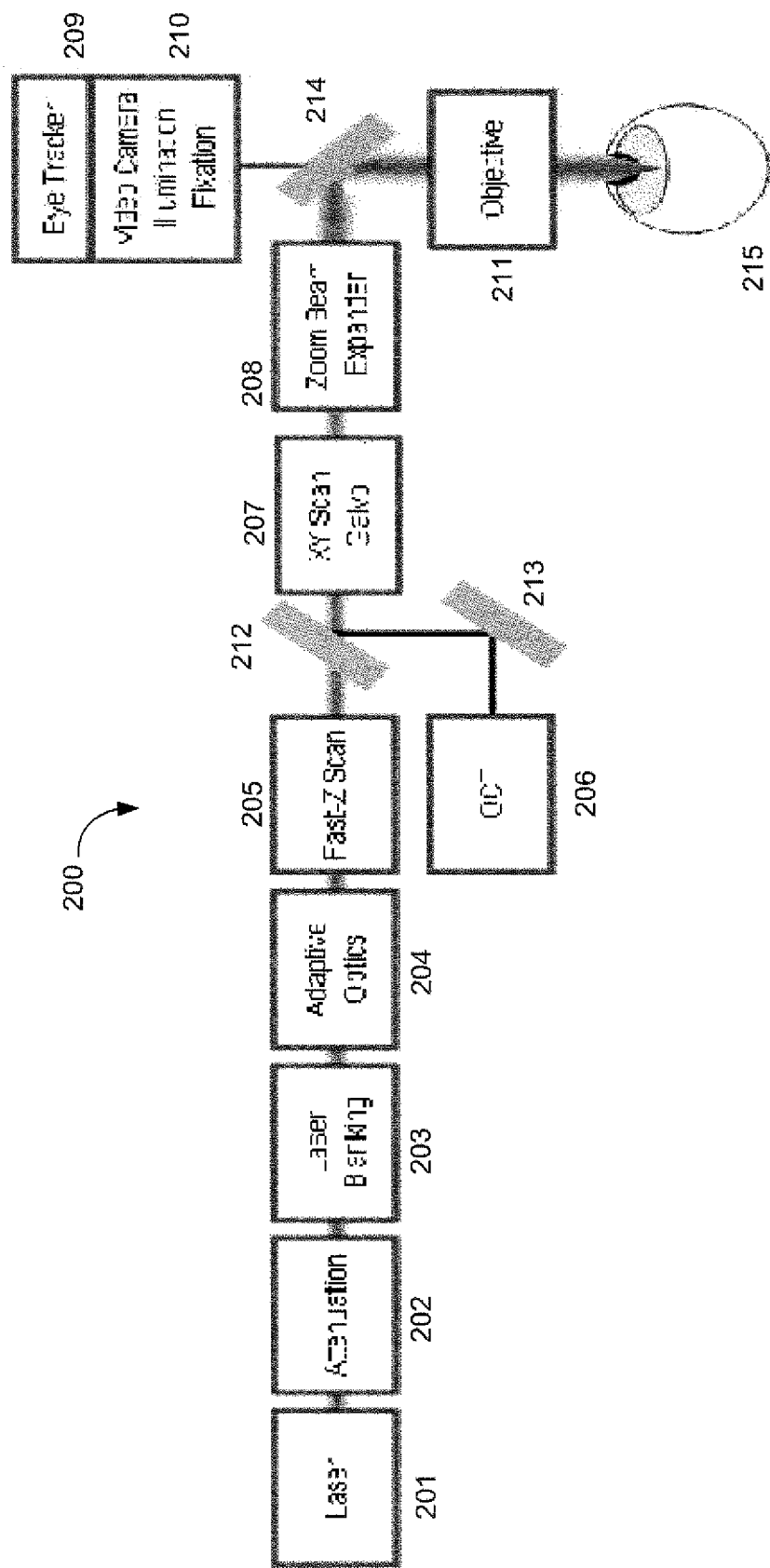
FIG. 2 is a general diagram of the components employed in the ultra-short pulsed ocular laser surgical system that does not require eye docking.

FIG. 2 illustrates an alternate version of a system that may be employed with the present design. The eye 215 of the patient is subjected to ultra-short pulsed laser surgery. Eye movement may result from oculomotor systems (e.g. saccadic eye movements), head movement, heartbeat, and other sources. Eye movement may be in six degrees of freedom, including X, Y, and Z translations as well as rotations including X-roll ($\Phi_x$), Y-roll ($\Phi_y$), and cyclotorsional angular rotation ($\Psi_C$). From FIG. 2, laser 201 includes a laser engine configured to provide an ultra-short pulsed laser beam. Attenuator 202 attenuates the beam, while laser blanking element 203, also known as a fast shutter, turns the laser beam on and off at selected times to achieve the necessary cutting profile. Adaptive optics 204 are variable optics used to correct waveform aberration caused by the air-cornea interface that materialize in the absence of eye docking components. In one embodiment, a multiple part reflective surface or mirror is employed in adaptive optics 204. The response frequency of the adaptive optics 204 corrects wavefront aberration when the laser is not raster scanning across the eye but is performing a desired surgical procedure, such as chopping a cataractous lens.

Fast-z scan optics 205 adjusts position and focus of the laser beam to actively follow the z (depth) position change due to eye movement. Z position is of particular interest in ultra-short pulsed laser surgery. Gross z position for the laser focus may be controlled by the slow motion z scan optics, such as the zoom beam expander 208 or the objective module 201, while the fine z position is generally addressed using fast-z scan optics. In general, the fast-z scan optics 205 include lenses providing a numerical aperture configured to provide the focal spot at a desired depth in the eye 215. The fast-z scan optics operate rapidly due to the changes that can result in depth and are generally fast enough to compensate for the z (depth) change due to saccadic movements resulting from by X-roll ($\Phi_x$) and Y-roll ($\Phi_y$).

OCT (Optical Coherence Tomography) module 206 employs OCT technology to capture three dimensional images of biological tissue, such as ocular tissue, using interferometric techniques. OCT module 206 generally comprises optics and processing components configured to receive and view images of eye 215, particularly depth images, and to provide depth or z information for further processing. OCT module 206 generally provides a deeper penetration into the biological material than other scanning technologies. As a result, the depth (z) information obtained by OCT module 206 is enhanced as compared with other devices, such as eye trackers. In a typical implementation, OCT module 206 may have an accuracy of approximately 10 micrometers, which is a function of the z-range of the laser affected zone of the ultra-short pulsed laser pulse. In addition to the depth measurement, the OCT module also provides the topography and necessary structure of the eye so that the system can calculate the wavefront aberration at the focus and use this quantity to control the deformable mirror (adaptive optics) to correct the wavefront error.

XY Scan Galvanometer 207 controls the X-Y position of laser focus and includes components that receive a current and move a mirror or reflective surface to provide proper X-Y beam positioning. The XY Scan Galvanometer 207 has a latency time sufficient to be actively adjusted to follow saccadic eye movements. Zoom beam expander 208 expands the beam received from the XY Scan Galvanometer 207 and provides the beam to objective 211, comprising a lens arrangement that focuses and directs the beam to the eye 215.

Light energy from the eye passes back through the objective and to beamsplitter 214, which directs light energy to zoom beam expander 208 and video camera illumination fixation element 210. Illumination fixation element 210 provides adjustable fixation direction. Such fixation facilitates alignment of a high grade cataractous eye with desired surgical direction and may reduce gross eye movements.

Eye tracker 209 in this arrangement is a camera-based device that measures five degrees of freedom of the eye 215, including X, Y, X-roll ($\Phi_x$), Y-roll ($\Phi_y$), and cyclotorsional angular rotation ($\Phi_C$) of the eye 215. Eye tracker 209 measures movement of the eye using a video camera and outputs eye position, typically the values noted, X, Y, $\Phi_x$, $\Phi_y$, and $\Psi_C$, to a system controller (not shown) Latency time, i.e. time between movement of the eye 215 and measurement output from eye tracker 209 to the system controller is preferably small. One example of operation may be the eye tracker 209 operating at a frame rate of 1000 Hz, with a latency time of less than 1.0 milliseconds. A high degree of accuracy is preferable, such as in the single digit micrometer range and angular accuracy in the hundredths of degree range. Such values tend to be a function of the distance range of the tissue affected zone affected by the laser pulse, and more particularly the distance between the eye 215, objective 211, and the video camera illumination fixation element 210 and eye tracker 209. A smaller distance between these elements may enable a looser tolerance range.

Light energy provided to beamsplitter 214 is also provided to zoom beam expander 208, XY Scan Galvanometer 207, and to beam splitter 212, which deflects the light energy representing the image of the eye 215 to reflective surface 213 and OCT module 206 for the OCT processing discussed above.

As noted, a system controller is provided but not shown in FIG. 2, wherein the controller analyzes X, Y, Z, $\Phi_x$, $\Phi_y$, and $\Psi_C$ data outputs, including recent histories, and derives the eye position, velocity, and acceleration values of eye 215. The controller may account for known or viewed behavior and may be employed as discussed herein to predict eye trajectory during a forthcoming time period. The system controller determines and seeks to compensate for the error between the laser focus trajectory and the eye movement/position for the desired laser pattern. The system controller provides commands as to how the beam delivery system (XY Scan Galvanometer 207, fast-z scan optics 205, eye fixation light 210, and adaptive optics 204) are adjusted and timing of opening and closing of the laser blanking shutter in laser blanking module 203.

For a desired cut profile, an enhanced laser pattern may be employed to increase tolerance of position errors between intended position of the laser and actual position of the laser. Such enhanced laser patterns may be similar to those described in U.S. Patent Application Ser. No. 61/753,319, entitled "Robust Laser Cutting Methods for Ophthalmic Surgery," filed Jan. 16, 2013, inventors Hong Fu and John Tamkin, which is incorporated here by reference.

Figure 3:
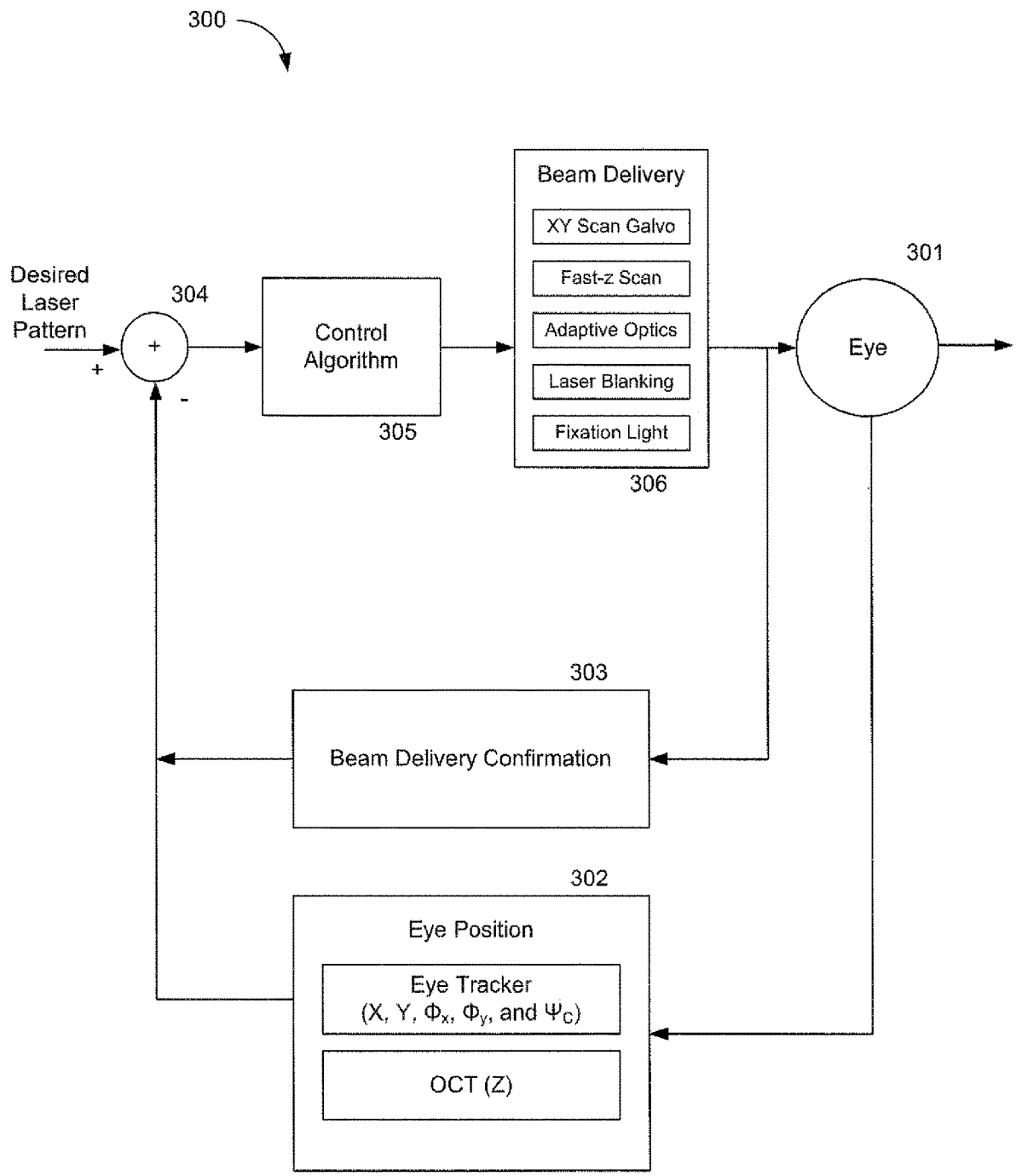
FIG. 3 illustrates the control arrangement of the present design seeking to employ the ultra-short pulsed laser at a desired position of the eye.

FIG. 3 provides a representation of a control module 300 employed in the present device, which may take the form of a program provided in the system controller. From the left side of FIG. 3, the desired laser pattern or current position of the laser beam relative to the eye is input and represents the reference value of the present design. The output is the actual position of the laser beam on the eye, and the eye position is measured by both eye tracker 209 (X, Y, $\Phi_x$, $\Phi_y$, and $\Psi_C$) and OCT module 206 (Z), shown as eye position module 302. Laser beam position is determined by a beam delivery confirmation module 303. Beam delivery confirmation module 303 represents any device or arrangement that determines position of the beam on the eye, and may include simple monitoring at the input or output of objective 211, out of zoom beam expander 208, and/or observation by eye tracker or other external devices. Output of the beam delivery confirmation module 303 is the position of the beam. Both this beam position and the eye position are fed back to summation element 304, where output of summing element 304 is the error between the desired position of the beam on the eye (reference) versus the actual position of the beam on the eye.

Control algorithm 305 receives the error and other pertinent information (historic eye position, eye movement profiles, expected future laser pattern, and so forth) and provides control values to beam delivery components 306 to direct the beam to the appropriate position on the eye. Beam delivery components 306 include X-Y Scan Galvanometer 207, Fast-z scan module 205, adaptive optics 204, laser blanking module 203, and fixation light 210. These components are configured to have alterable parameters (position, focus, timing, and so forth) controllable by the controller 305 to effectuate the desired position of the beam on the eye 301.

Figure 4:
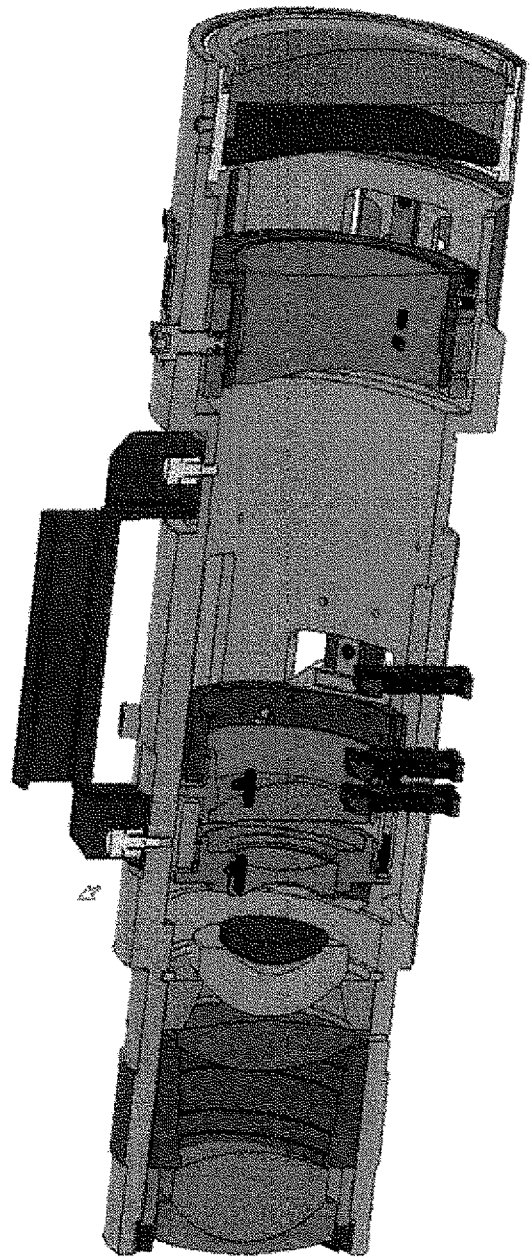
FIG. 4 is a typical zoom beam expander employed with the present design.
Figure 4:
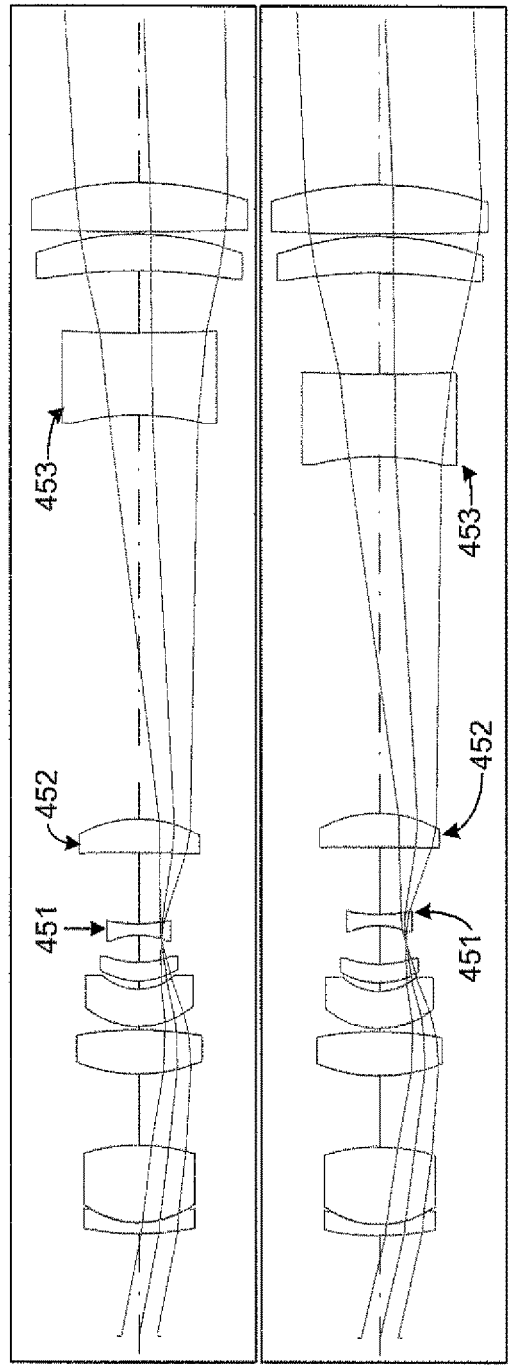

FIG. 4 illustrates a zoom beam expander that may be employed with the present design as zoom beam expander 208. The zoom beam expander 208 includes a number of lens elements that can be repositioned to effectuate expansion of the incoming beam. View 401 shows various lens elements with middle elements 451, 452, and 453 positioned to provide a beam for use in a capsulotomy at a 6.0 millimeter depth. View 402 provides various lens elements with middle elements 451, 452, and 453 positioned for a flap creation procedure.

Figure 5:
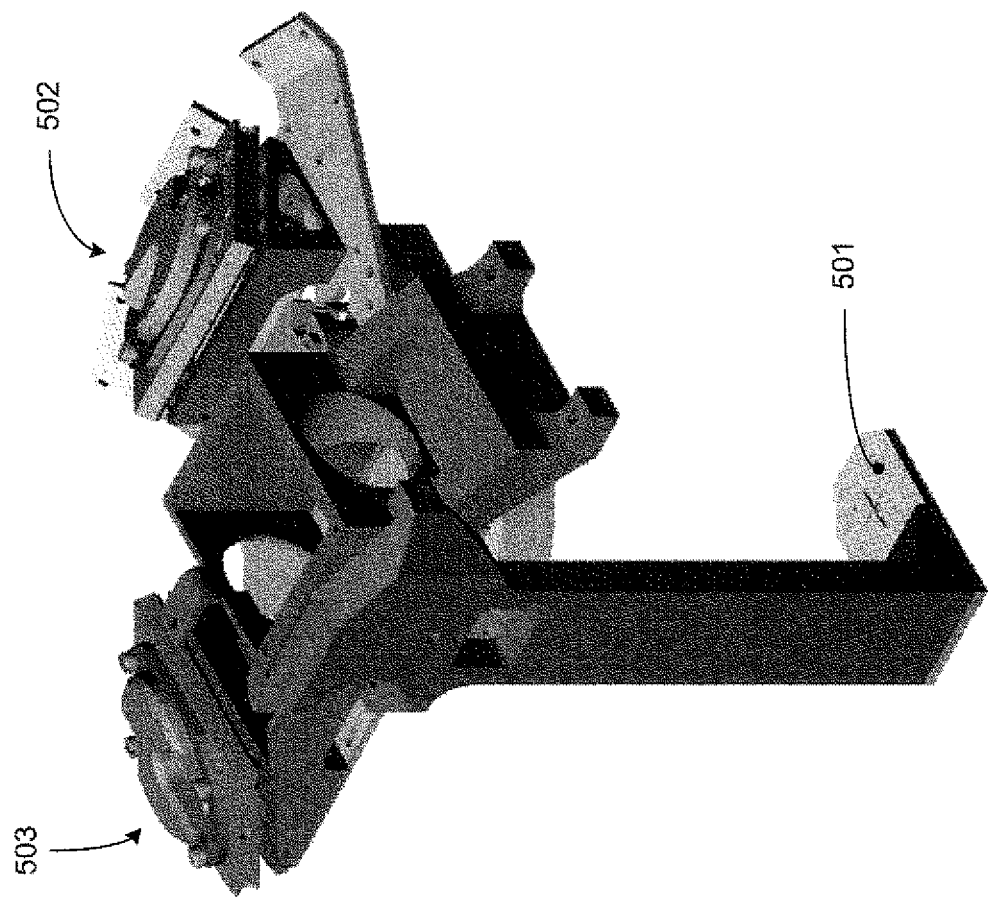
FIG. 5 shows a typical setup of an eye tracker in accordance with the present design.
Figure 6:
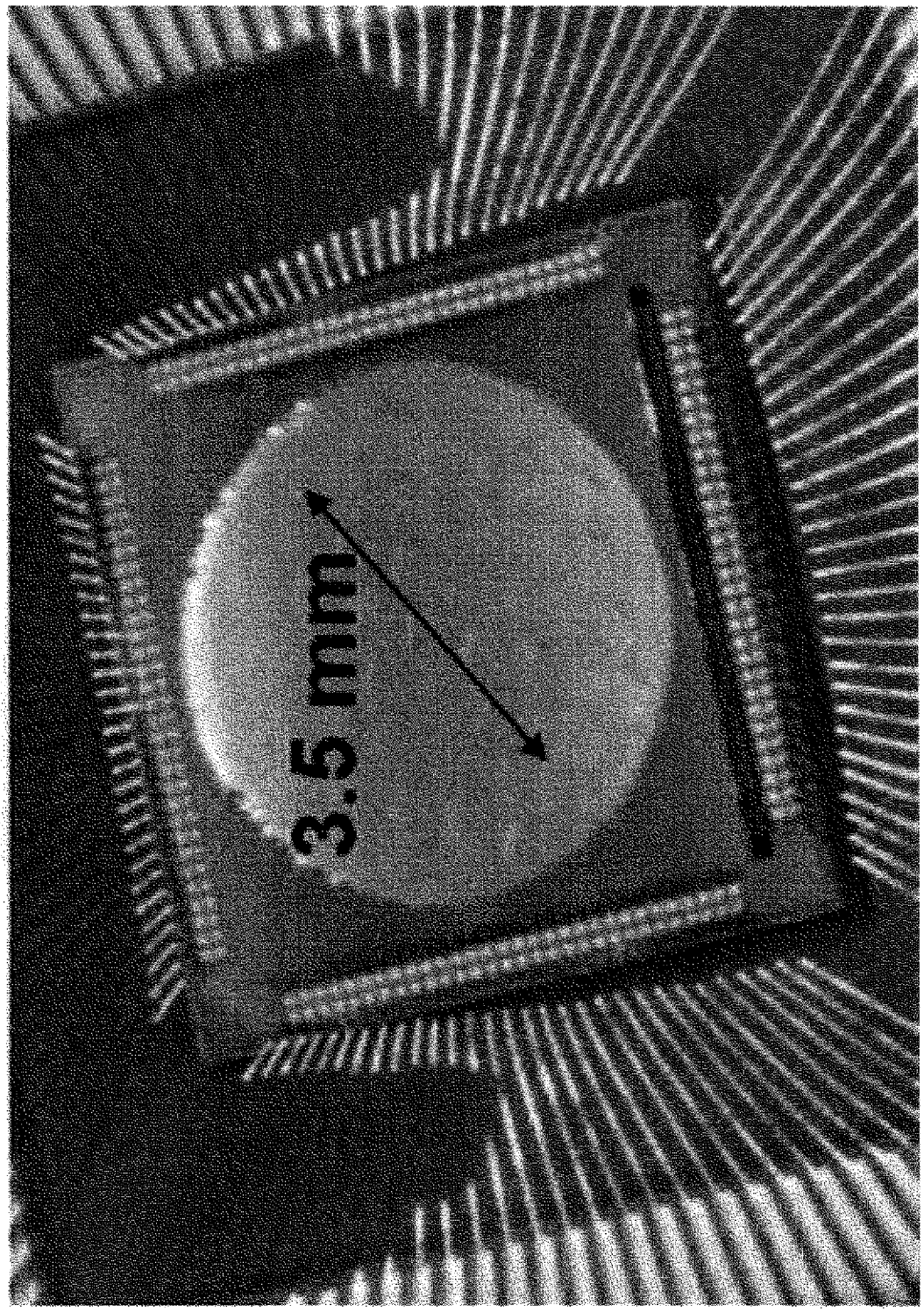
FIG. 6 illustrates adaptive optics that may be employed in the present design.

FIG. 5 shows an example of an eye tracker arrangement, showing alignment fixture 501 and two cameras 501 and 502 positioned to view the eye from a distance. The adaptive optics 204 may include a MEMS deformable mirror, shown in FIG. 6 and in this embodiment having a 3.5 millimeter diameter. Control is provided for each surface in the deformable mirror such that the various honeycomb or hexagonal elements can be repositioned as desired to effectuate laser positioning and focus commanded by the system controller.

In the arrangement shown in FIGS. 1-6, there is provided a system that performs eye tracking and ultra-short pulsed laser surgery without the use of a docking mechanism, wherein eye tracking provides sensing of five degrees of freedom for the subject eye and an OCT system provides the sixth degree of freedom, namely depth. The present design also employs adaptive optics, such as a deformable mirror, during ocular surgery wherein the adaptive optics are employed to measure the wavefront, adjust at least one reflective surface and compensate for patient movement during the surgical procedure. Finally, a control system is provided that employs measurements from the eye tracker and the OCT system for position of the eye as well as position of the laser beam and compensates for errors in these positions by adjusting components of the system, such as XY Scan Galvanometer, a Fast-z scan module, adaptive optics, a laser blanking module, and/or a fixation light. The resultant device enables robust ultra-short pulsed laser surgery without the need for docking the eye of the patient.

Contact (Scleral) Ring with Fiducial Marker

As noted, one issue with eye tracking is the difficulty in discerning different attributes and/or positions of an eye. Different eyes exhibit different visual characteristics, and issues may arise such as a gradual change in color between the iris, cornea, and/or sclera, and different refractive qualities to different eyes that can be difficult to discern using an eye tracker.

In connection with the foregoing system, or for use with other systems employing eye tracking, the present design may employ a device that places known and readily discernible markers in connection with the eye for the express purpose of tracking the position of the eye.

Figure 7A:
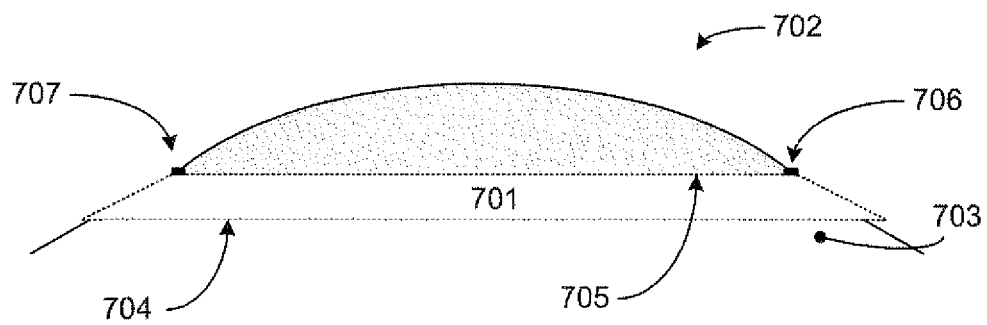
FIG. 7A is a side view of an eye with a scleral ring provided.

FIG. 7A illustrates a first embodiment of the present aspect of the design. In FIG. 7A, scleral ring 701 is a hollow ring that fits over the eye 702 and contacts the sclera 703. No material is provided in the center region, and thus the pupil, iris, and cornea in a typical patient is unobscured and open for purposes of eye surgery. Under typical situations, the eye, lid, and ocular fluid keep the scleral ring 701 in a fixed position relative to the eye, i.e. the scleral ring 701 does not slide when the eye moves.

The scleral ring 701 is similar to a traditional contact lens in form and construction, but may be made of a slightly more rigid material to hold the scleral ring 701 in place. Further, the construction of the scleral ring 701 may be flared slightly, with a base 704 that is slightly larger than an average eye while the upper edge 705 is sized to tightly contact the sclera of the patient in order to facilitate holding the entire scleral ring 701 on the sclera 703. The base 704 or posterior surface material may be compliant to allow the scleral ring to conform to the natural curvature of the eye, and the scleral ring 701 may self-center in a manner similar to a contact lens.

In the embodiment of FIG. 7A, markers 706 and 707 are provided. These markers may be dark markings in or on the scleral ring 701 that may be discerned from a distance and may be resolved by an eye tracker, while the remainder of the scleral ring is either a contrasting color, such as white in contrast to black, or clear/transparent similar to a contact lens. A single marker or multiple markers may be provided, sometimes called fiducial marks or fiducials, and the marker or markers may take any form usable and discernible by an eye tracking system.

Figure 7B:
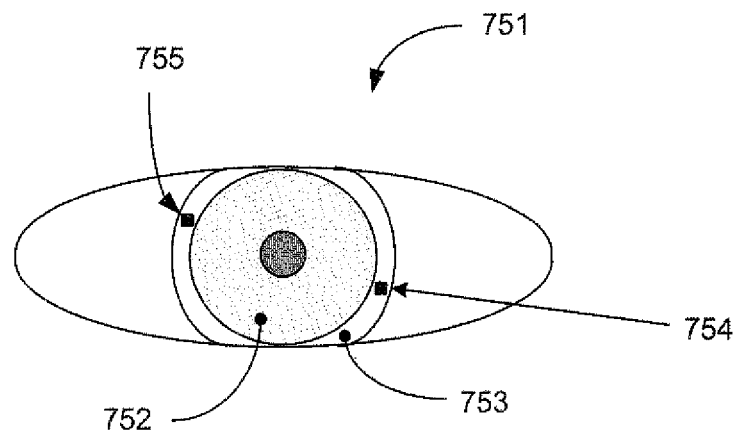
FIG. 7B is a front view of an eye with a scleral ring provided in accordance with one embodiment of the present design.

FIG. 7B illustrates a front view of an eye 751 including scleral ring 753 positioned in association with cornea 752. No covering exists over cornea 752, i.e. the center of scleral ring 753 is a void or open space enabling ultra-short pulsed laser surgery on the cornea. Fiducial markings 754 and 755 are provided, in this arrangement squares having a dark coloring.

Figure 8:
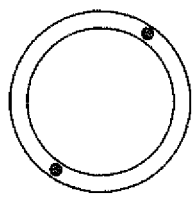
FIG. 8 illustrates a variety of potential scleral ring designs.
Figure 8:
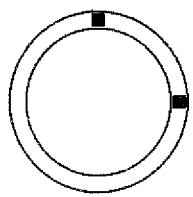
Figure 8:
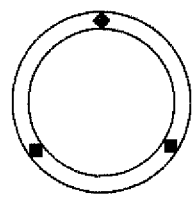
Figure 8:
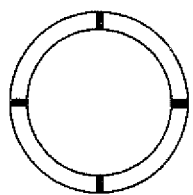
Figure 8:
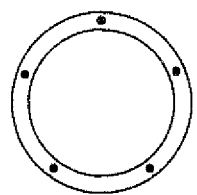
Figure 8:
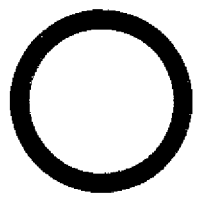
Figure 8:
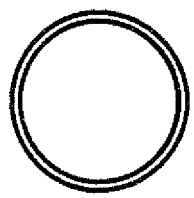
Figure 8:
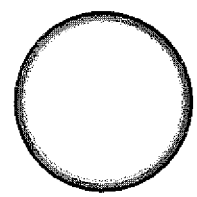
Figure 8:
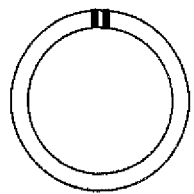
Figure 8:
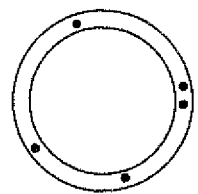

FIG. 8 shows various patterns that may be employed in a scleral ring in accordance with the present design, including two marks 180 degrees apart on ring 801, two marks 90 degrees apart on ring 802, three equidistant marks on ring 803, four equidistant marks on ring 804, five equidistant marks on ring 805, a solid ring 806, rings with dark outer and inner rings on ring 807, a ring with a dark inner ring and a lighter center ring and an even lighter center ring in ring 808, two points positioned in close proximity in ring 809, and five points randomly distributed in ring 810. As may be appreciated, any type of mark or fiducial mark arrangement may be employed that serves to facilitate eye tracking using an eye tracking mechanism.

When used in connection with the system described above employing an eye tracker, the scleral ring 701 can provide enhanced certainty of patient eye position and may be less likely to result in positioning errors of the laser beam clue to patient movement or eye feature issues. Use of a scleral ring including fiducials tends to significantly reduce time required for processing the image of the eye and enables robust resolution of the position and orientation of the eye at any given time.

In one embodiment, the scleral material comprises material similar to contact lenses, including but not limited to polymers, RGP materials, hydrogels, and the like. With respect to sizing and fit, the scleral ring is formed to allow a contoured fit to the sclera for a general set of the population. One alternative is to provide a pre-made set of scleral rings that match a specific set of patients. Using contact lens type materials to form the scleral ring, external forces on the cornea are removed, intraocular pressure is reduced, and corneal wrinkle risk can be decreased as compared to docking arrangements previously employed.

Fluid Filled and Compliant Contact Lenses

During laser cataract surgery or certain portions of the LASIK procedure, such as those employing a ultra-short pulsed laser as described herein, docking of the patient's eye is typically provided using a conical patient interface including a suction ring and a flat applanating lens. A curved patient interface or a liquid patient interface may be used for docking to ease some of the discomfort. Again, as mentioned before conventional docking and applanation procedures can cause patient discomfort at the very least, and may in some instances, increase intraocular pressure and/or cause corneal wrinkles. A further issue, particularly in the case of an eye tracker being used with an eye subjected to ultra-short pulsed laser surgery, is a difference in the index of refraction encountered between the air and the eye material. The drastic difference in refractive index can in certain instances provide less than ideal laser cuts and the laser beam can reflect or scatter when contacting ocular tissue.

Figure 9:
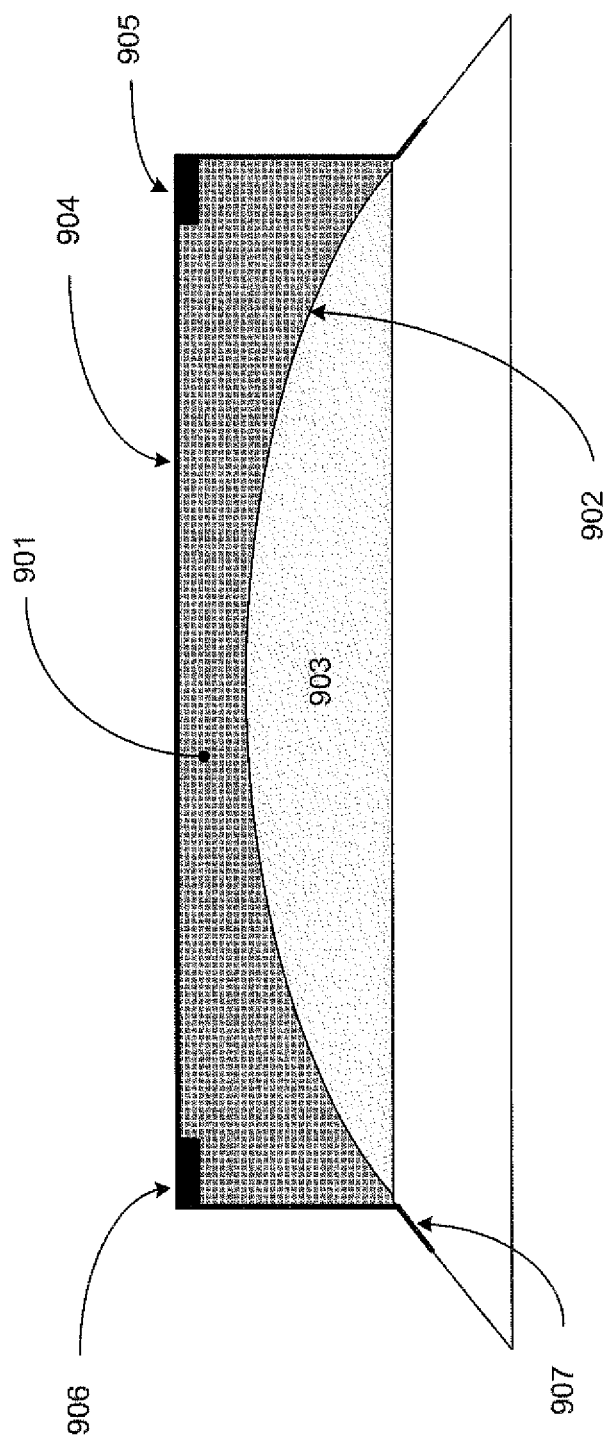
FIG. 9 is a side view of an eye employing a compliant contact lens for use in ultra-short pulsed laser ocular surgery including fiducial markings.

To address these issues, the present design may employ a compliant contact lens as shown in FIG. 9. As with other designs provided herein, the design of FIG. 9 requires no docking or physical patient interface. The device of FIG. 9 may be employed with or without a scleral ring, and in the particular arrangement shown in FIG. 9, markers or fiducials are illustrated. The compliant contact lens 901 includes a posterior surface or inner edge 902 curved to conform either to the particular patient's eye, or to an average or expected patient profile, such as the mean radius of curvature of the general population. Compliant contact lens 901 fits over the cornea 903 and comprises a flat or relatively flat exterior surface 904. The compliant contact lens 901 may be formed of a uniform single material construction or a multi-part construction to facilitate patient comfort, tracking of the position of the eye, and ability of the laser to successfully perform the desired cutting pattern.

The compliant contact lens 901 may be formed of or include a transparent or translucent material having an index of refraction that matches or is very close to that of the cornea, in humans approximately 1.37, where the compliant contact lens 901 is penetrable by an ultra-short pulsed laser. The posterior surface or inner edge 902 may be made from a material identical to or different from the rest of compliant contact lens 901 to enable the lens to conform to the natural curvature of the patient's eye and may self center in a manner similar to a conventional contact lens. The inner edge 902 may be provided with additional material or a fluid may be applied between the cornea 903 and the inner edge 902, or between the cornea 903 and material placed between the inner edge 902 and the cornea 903. The material used for the exterior surface or relatively flat exterior surface 904 may differ from the other components, layers, or parts of compliant contact lens 901 to facilitate laser delivery.

As with the scleral ring discussed above, fiducials or markings provided, such as fiducials 905 and 906, may vary but in general may take any for as discussed, i.e. providing one or multiple markings, rings, or other eye tracker discernible characteristics. As the flat exterior surface is a large surface rather than a ring, other discernible markings or fiducials may be provided, including but not limited to lines, arrows, different color markings, curves, and virtually any marking imaginable. As shown in FIG. 9, either a support arrangement or a complete scleral ring 907 may be provided at the base of compliant contact lens 901, separate from or adjoined to compliant contact lens 901. Such a support arrangement or scleral ring 907 is not required but can provide support and stability when deployed in the eye.

Figure 10:
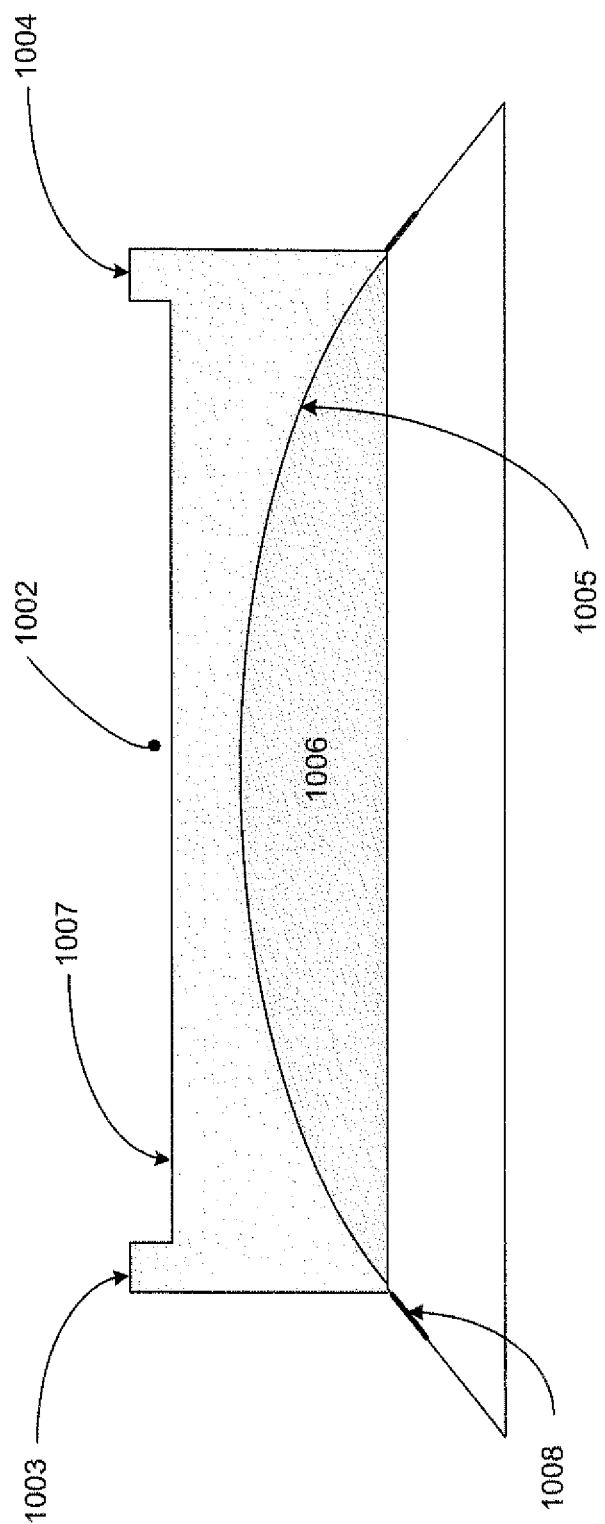
FIG. 10 is a side view of an eye employing compliant contact lens for use in ultra-short pulsed laser ocular surgery with a low force docking construction.

As an alternative to docking as well as an alternative to the design of FIG. 9, compliant contact lens employing near zero force docking may be provided as shown in FIG. 10. From FIG. 10, compliant contact lens 1001 does not include markings or fiducials, but rather includes a cavity 1002 formed by exterior raised edge or edges 1003, 1004 that may be docked with a lesser force than a traditional patient interface docking arrangement, such as one employing a suction ring and flat applanating lens. The device of FIG. 10 may be employed with or without a scleral ring. The compliant contact lens 1001 includes a posterior surface or inner edge 1005 curved to conform either to the eye of the particular patient, or to an average or expected patient profile, such as the mean radius of curvature of the general population. Compliant contact lens 1001 fits over the cornea 1006 typically includes a flat or relatively flat exterior surface 1007.

Compliant contact lens 1001 may be formed of a uniform construction or a multi-part construction. The compliant contact lens 1001 may include a transparent or translucent material having an index of refraction that matches or is very close to that of the cornea, where the compliant contact lens 1001 is penetrable by an ultra-short pulsed laser. The posterior surface or inner edge 1005 may be made from a material identical to or different from the rest of compliant contact lens 1001 to enable the lens to conform to the natural curvature of the patient's eye and may self center in a manner similar to a conventional contact lens. The inner edge 1005 may be provided with additional material or a fluid may be applied between the cornea 1006 and the inner edge, or between the cornea and material placed between the inner edge 1005 and the cornea 1005. Again, the material used for the exterior surface or relatively flat exterior surface 1007 may differ from the other components, layers, or parts of compliant contact lens 1001, and a support arrangement or scleral ring 1008 may be provided in a manner similar to that described with respect to the FIG. 9 design.

Figure 11:
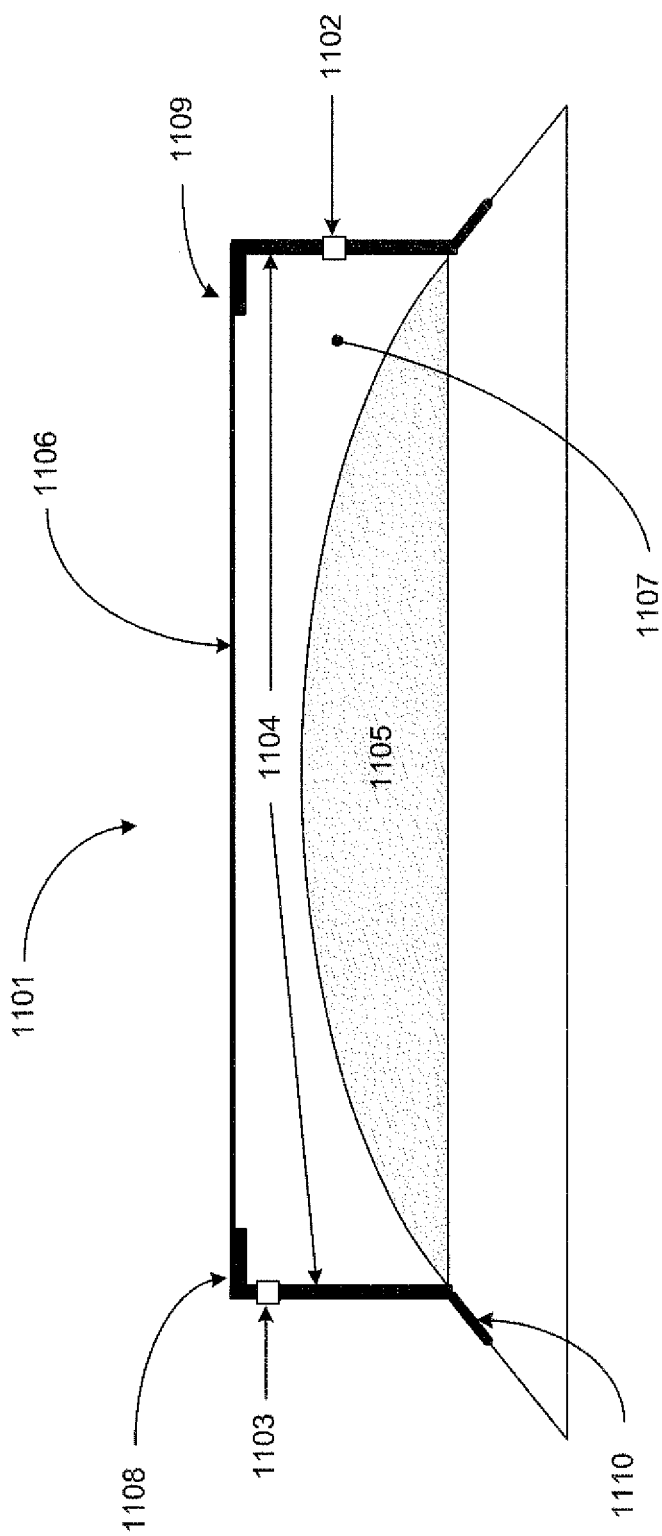
FIG. 11 illustrates a fluid-fillable contact lens for use in ultra-short pulsed laser ocular surgery including fiducial markings.

FIG. 11 illustrates an alternate embodiment of the present design including a fluid filled contact lens 1101 having an open area configured to receive fluid from, for example, entry point 1102 and exit from exit point 1103. The fluid filled contact lens 1101 includes sides 1104 sufficient to receive and maintain fluid, such as using a hard plastic or polymer, and rests primarily above cornea 1105. A certain distance is provided between an upper surface 1106 and cornea 1105 sufficient for fluid to collect. In certain instances, a vacuum may be formed by filling or partially filling the cavity 1107 formed by the fluid filled contact lens 1101. Fiducials or markings may be provided, and in FIG. 11, fiducials are shown by darkened elements 1108 and 1109, but again, any form of marking discernible by an eye tracker may be employed. A support arrangement or scleral ring 1110 may be provided. In other words, the exterior side or sides 1104 may include at the base thereof a ring or element or elements 1110 used to hold the fluid filled contact lens 1101 in juxtaposition with the sclera, and this ring, element, or elements may comprise a scleral ring as described, or other appropriate device.

Unlike the design of FIGS. 9 and 10, the design of FIG. 11 does not have a posterior surface or inner edge, but instead provides fluid to gradually change index of refraction from air to fluid to cornea. Additionally, once fluid is introduced into cavity 1107, suction may be applied by reversing fluid flow, enabling the device to be physically fixed to the eye. The resultant suction force is applied over a larger area, reducing intraocular pressure.

Figure 12:
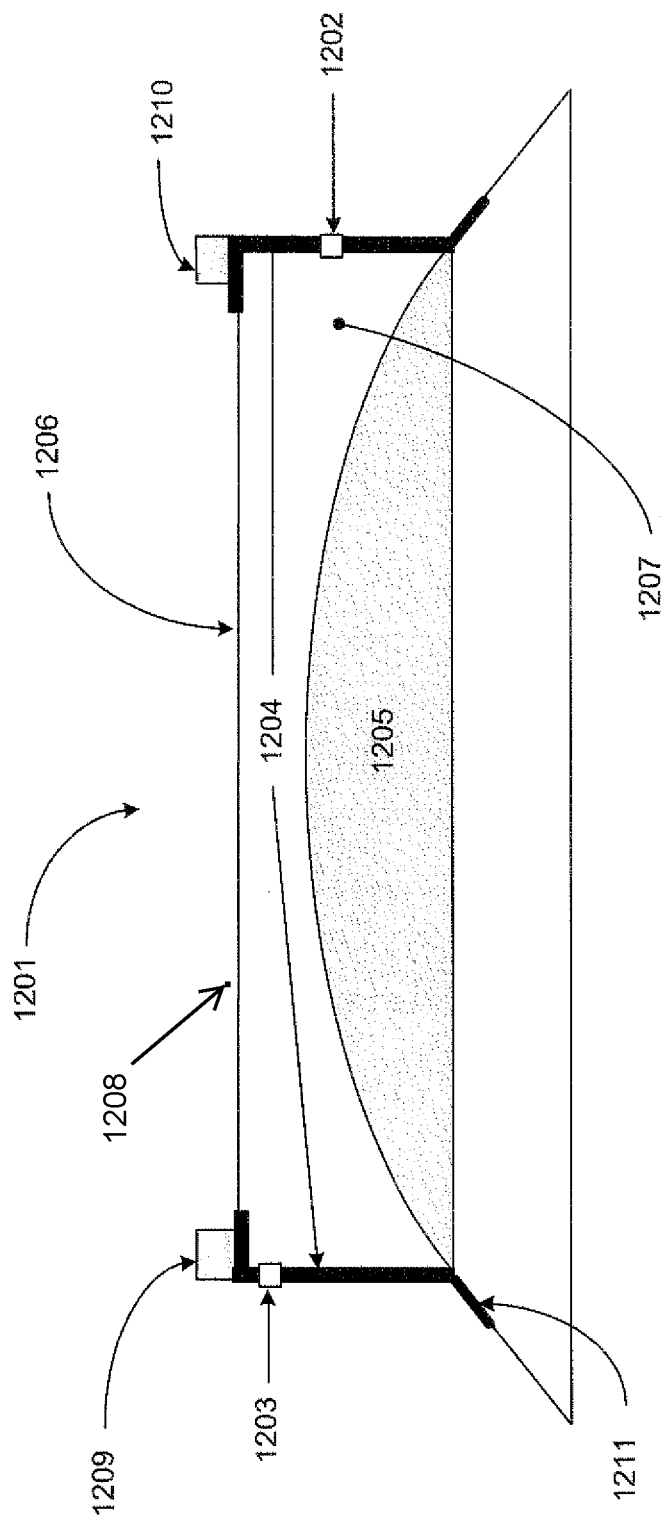
FIG. 12 shows a fluid-fillable contact lens for use in femtosecond laser ocular surgery with a low force docking construction.

FIG. 12 illustrates an alternate embodiment of a fluid filled contact lens 1201 that employs a low or near zero force docking function. As with the design of FIG. 11, fluid filled contact lens 1201 has an open area configured to receive fluid from, for example, entry point 1202 and exit from exit point 1203. The fluid filled contact lens 1201 includes side(s) 1204 sufficient to receive and maintain fluid, such as a generally circular side constructed of a hard plastic or polymer, and rests primarily above cornea 1205. A certain distance is provided between an upper surface 1206 and cornea 1205 sufficient for fluid to collect. In certain instances, a vacuum may be formed by filling or partially filling the cavity 1207 formed by the fluid filled contact lens 1201. In this arrangement, fiducials or markings are typically not provided, but are not expressly prohibited.

Compliant contact lens 1201 includes a cavity 1208 formed by exterior raised edge or edges 1209, 1210 that may be docked with a lesser force than a traditional patient interface docking arrangement, such as one employing a suction ring and a flat applanating lens. The device of FIG. 12 may be employed with or without a support arrangement or scleral ring 1211.

While shown in FIGS. 11 and 12 with entry point 1102 above exit point 1203 and on opposite sides of fluid filled contact lens 1101, for example, such positioning is not required and the entry and exit points may be placed elsewhere on or in fluid filled contact lens 1201 and 1202, and fluid may be provided and/or expelled or drawn through a slit or larger opening than is illustrated. The intent is to provide and draw fluid in an efficient manner while effectuating the functionality, including ultra-short pulsed laser surgical functionality, disclosed herein.

In these embodiments, the device shown comprises a contact lens having a relatively flat exterior surface configured to provide a buffer region between air and the eye to decrease index of refraction issues. The device includes a piece configured to fit over a cornea of a patient with a curved posterior surface and a flat or relatively flat anterior surface, the piece dimensioned to cover the cornea of the patient's eye. In one embodiment, markings or fiducial markings are provided, while in another embodiment a cavity is provided using the anterior surface that facilitates a low force docking to the eye. A second embodiment comprises a generally hollow contact lens comprising an anterior surface adjoining at least one exterior wall with fluid entry and exit openings provided, the anterior surface sized to cover a cornea of a patient. The generally hollow contact lens may include markings or fiducials, and the generally hollow contact lens is configured to be filled with fluid that contacts the cornea of the patient and facilitates index of refraction transition from air to fluid to cornea. In an alternate embodiment, a cavity is provided using the anterior surface that facilitates a low force docking to the eye.

Thus according to one embodiment, there is provided an apparatus for performing eye docking free laser surgery. The apparatus comprises an ultra-short pulsed femtosecond laser engine configured to provide a laser beam, optics configured to direct the laser beam to an undocked eye of a patient, an eye tracker configured to measure five degrees of freedom of movement of the undocked eye of the patient, an optical coherence tomography module configured to measure depth of the undocked eye of the patient, and a controller configured to control laser beam position on the undocked eye of the patient toward a desired laser pattern based on depth of the undocked eye of the patient measured by the optical coherence tomography module and the five degrees of freedom of movement of the undocked eye of the patient measured by the eye tracker. The apparatus may include an adaptive optics device configured to compensate for wavefront error based on topography of the undocked eye measured by the optical coherence tomography module.

According to another embodiment, there is provided a method for performing eye docking free laser surgery. The method comprises providing an ultra-short pulsed laser beam, directing the laser beam to an undocked eye of a patient, measuring five degrees of freedom of movement of the undocked eye of the patient using an eye tracker, measuring depth of the undocked eye of the patient using an optical coherence tomography module, and controlling laser beam position on the undocked eye of the patient toward a desired laser pattern based on depth of the undocked eye of the patient measured by the optical coherence tomography module and the five degrees of freedom of movement of the undocked eye of the patient measured by the eye tracker. The method may include compensating for wavefront error based on topography of the undocked eye measured by the optical coherence tomography module.

A further embodiment includes a scleral ring configured to fit over a cornea of a patient, the scleral ring comprising an exterior circular ring formed with a circular opening therein. The scleral ring comprises at least one fiducial marking discernible from a distance by an eye tracking device.

A further embodiment comprises a lens configured to fit over an eye of a patient and substantially cover the cornea of the patient, the lens comprising a relatively flat anterior surface and a curved posterior surface. The lens is configured to receive a ultra-short pulsed laser beam and facilitate performance of ocular surgery by providing an index of refraction closer to that of ocular tissue than air. An alternative embodiment includes a lens configured to fit over an eye of a patient and substantially cover the cornea of the patient, the lens comprising a relatively flat anterior surface and a chamber configured to maintain fluid in association with the eye of the patient. The lens is configured to deliver a laser beam to the eye of the patient and facilitate performance of ocular surgery by providing an index of refraction closer to that of ocular tissue than air.

Those of skill in the art will recognize that the step of a method described in connection with an embodiment may be interchanged without departing from the scope of the invention. Those of skill in the art would also understand that information and signals may be represented using any of a variety of different technologies and techniques. For example, data, data packets, packet groups, instructions, commands, information, signals, and bits that may be referenced throughout the above description may be represented by voltages, currents, electromagnetic waves, magnetic fields or particles, optical fields or particles, or any combination thereof.

Those of skill in the art would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of embodiments of this invention.

An apparatus implementing the techniques or circuits described herein may be a stand-alone device or may be part of a larger device. In one or more exemplary designs, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer.

Although embodiments of this invention are described and pictured in an exemplary form with a certain degree of particularity, describing the best mode contemplated of carrying out the invention, and of the manner and process of making and using it, those skilled in the art will understand that various modifications, alternative constructions, changes, and variations can be made in the ophthalmic interface and method without departing from the spirit or scope of the invention. Thus, it is intended that this invention cover all modifications, alternative constructions, changes, variations, as well as the combinations and arrangements of parts, structures, and steps that come within the spirit and scope of the invention as generally expressed by the following claims and their equivalents.

What is claimed is:

1. A surgical laser system configured to deliver an ultra-short pulsed laser beam to a patient's eye comprising:
 a lens configured to fit over an anterior surface of the patient's eye and cover a central portion of the cornea, the lens comprising a substantially flat anterior surface and a chamber configured to cooperate with the anterior surface of the patient's eye to maintain fluid in the chamber, the lens further comprising a scleral ring at a base of the lens to support the lens on the eye, wherein the scleral ring is formed of a compliant material, the scleral ring having a first side and a second side opposite to each other, the first side defining a continuous ring-shaped area, the scleral ring configured to have the continuous ring-shaped area of the first side fully contact the anterior surface of the eye, wherein the lens is free of other surfaces that contact the anterior surface of the eye;
 wherein the lens is configured to deliver an ultra-short pulsed laser beam to the eye of the patient and facilitate performance of ocular surgery by providing an index of refraction closer to that of ocular tissue than air.

2. The system of claim 1, wherein the lens is configured to receive fluid via a first fluid opening and disperse fluid via a second fluid opening, wherein reversing fluid flow from the chamber provides a level of suction maintaining the lens on the eye of the patient.

3. The system of claim 1, wherein the lens comprises at least one fiducial marking.

4. The system of claim 1, wherein the lens comprises at least one edge formed adjacent the anterior surface and forming a cavity, the at least one edge configured to enable docking of the lens to a patient interface.

* * * * *